United States Patent [19]
Boukhny et al.

[11] Patent Number: 5,938,677
[45] Date of Patent: Aug. 17, 1999

[54] CONTROL SYSTEM FOR A PHACOEMULSIFICATION HANDPIECE

[75] Inventors: Mikhail Boukhny, Laguna Beach; Ahmad Salehi, Irvine, both of Calif.

[73] Assignee: Alcon Laboratories, Inc.

[21] Appl. No.: 08/950,162

[22] Filed: Oct. 15, 1997

[51] Int. Cl.$^6$ .............................. A61B 17/32; H03L 7/00; H01L 41/04
[52] U.S. Cl. ............................. 606/169; 310/316; 331/16
[58] Field of Search ........................... 310/311, 316–322, 310/36; 318/631, 636, 638; 331/1 R, 13, 16, 154; 606/1, 107, 167, 169; 604/19, 22, 35

[56] References Cited

U.S. PATENT DOCUMENTS

| | | |
|---|---|---|
| 3,589,363 | 6/1971 | Banko et al. . |
| 3,964,487 | 6/1976 | Judson . |
| 4,126,137 | 11/1978 | Archibald . |
| 4,180,074 | 12/1979 | Murry et al. . |
| 4,223,676 | 9/1980 | Wuchinich et al. . |
| 4,428,748 | 1/1984 | Peyman et al. . |
| 4,525,790 | 7/1985 | Nakamura . |
| 4,535,759 | 8/1985 | Polk et al. . |
| 4,639,690 | 1/1987 | Lewis . |
| 4,642,581 | 2/1987 | Erickson . |
| 4,703,213 | 10/1987 | Gasler . |
| 4,808,948 | 2/1989 | Patel et al. . |
| 4,933,843 | 6/1990 | Scheller et al. . |
| 4,973,876 | 11/1990 | Roberts . |
| 5,045,054 | 9/1991 | Hood et al. . |
| 5,112,300 | 5/1992 | Ureche . |
| 5,139,509 | 8/1992 | Ficher et al. . |
| 5,160,317 | 11/1992 | Costin . |
| 5,279,547 | 1/1994 | Costin . |
| 5,331,951 | 7/1994 | Kepley . |
| 5,370,602 | 12/1994 | Kepley . |
| 5,407,525 | 4/1995 | Michel et al. . |
| 5,431,664 | 7/1995 | Ureche et al. . |
| 5,520,633 | 5/1996 | Costin ...................................... 606/169 |
| 5,536,272 | 7/1996 | Young et al. . |
| 5,808,396 | 9/1998 | Boukhny ................................. 606/169 |
| 5,852,794 | 12/1998 | Staggs . |

FOREIGN PATENT DOCUMENTS

| | | |
|---|---|---|
| 0328352 | 8/1989 | European Pat. Off. . |
| 0359217 | 3/1990 | European Pat. Off. . |
| 0424 685 | 5/1991 | European Pat. Off. . |
| 0424686 | 5/1991 | European Pat. Off. . |
| 0586882 | 3/1994 | European Pat. Off. . |
| WO 96 01701 | 1/1996 | WIPO . |

Primary Examiner—Glenn K. Dawson
Attorney, Agent, or Firm—Jeffrey S. Schira

[57] ABSTRACT

A system and method for tuning and controlling ultrasonic handpieces by varying the frequency of the drive signal that is fed to the handpiece by a discrete dither increment. A digital signal processor may be used to measure the response of the handpiece to the varying drive signal and compare these responses to determine the probable value of the actual series resonance. The output of the digital signal processor is used to generate control parameters embodied within an appropriate control signal, which is fed to the source of the drive signal in order to alter aspects of the drive signal.

8 Claims, 4 Drawing Sheets

CONTROL SYSTEM FOR A PHACOEMULSIFICATION HANDPIECE

This invention relates to a dithered control system and method for an ultrasonic device and more particularly for an ophthalmic phacoemulsification handpiece.

BACKGROUND OF THE INVENTION

A typical ultrasonic surgical device suitable for ophthalmic procedures consists of an ultrasonically driven handpiece, an attached hollow cutting tip, an irrigating sleeve and an electronic control console. The handpiece assembly is attached to the control console by an electric cable and flexible tubings. Through the electric cable, the console varies the power level transmitted by the handpiece to the attached cutting tip, and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece at its nodal points by relatively inflexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; and 4,922,902, the entire contents of which are incorporated herein by reference.

When used to perform phacoemulsification, the ends of the cutting tip and irrigating sleeve are inserted into a small incision of predetermined width in the cornea, sclera, or other location in the eye tissue in order to gain access to the anterior chamber of the eye. The cutting tip is ultrasonically vibrated along its longitudinal axis within the irrigating sleeve by the crystal-driven ultrasonic horn, thereby emulsifying upon contact the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the bore of the cutting tip, the horn bore, and the aspiration line and into a collection device. The aspiration of emulsified tissue is aided by a saline flushing solution or irrigant that is injected into the surgical site through the small annular gap between the inside surface of the irrigating sleeve and the outside surface of the cutting tip.

The horn assembly, including both piezoelectric and high endurance limit inert materials, used in ultrasonic handpieces must be carefully tuned for proper operation. As used herein, "tuning" refers to the process of finding and tracking the resonant frequencies of the handpiece operating under loaded or unloaded conditions. Operating the handpiece at a resonant frequency takes advantage of the crystal's energy storage capabilities, which occurs most efficiently at resonance. With proper tuning, the handpiece will store mechanical energy while operating unloaded and release this energy into the material being cut when loaded. As a consequence, for short periods of time, large amounts of energy can be directed into the material by the handpiece itself and not by the power source for the handpiece. This allows the power source to be designed to provide only the steady state power requirement of the transducer and not the loaded transients which can be many times higher.

Figure 1:
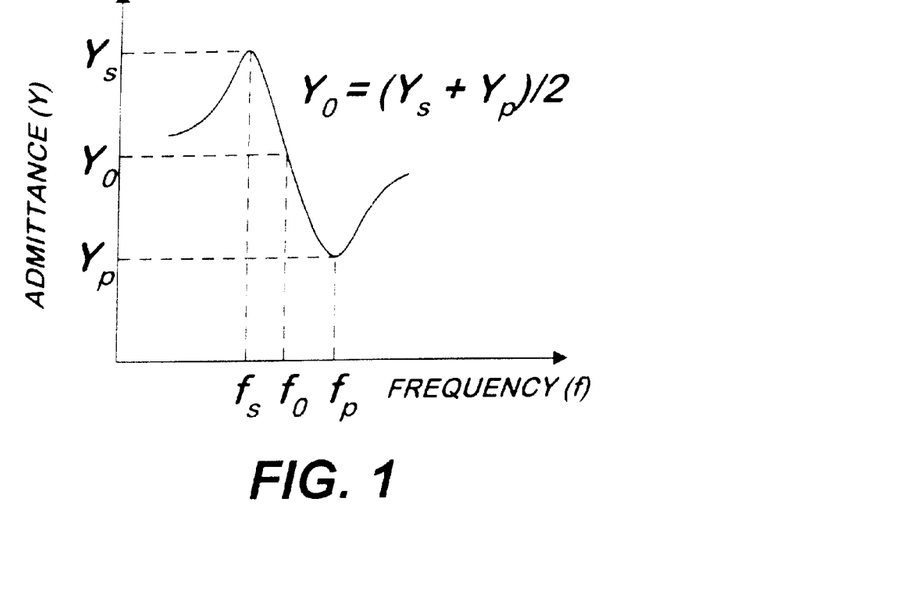
FIG. 1 is a graph of admittance versus frequency for a typical ultrasonic handpiece in the vicinity of the series and parallel resonances with a typical control admittance identified for a constant-admittance control system.

Conventional tuning and control systems determine the series and parallel resonant frequencies under a controlled loading condition, often in saline solution, before the handpiece is subjected to loads encountered during surgery. The handpiece is excited over a range of frequencies, one frequency at a time. The response of the handpiece to each frequency, measured as the admittance (the ratio of the drive current to the drive voltage), is recorded. A typical admittance versus frequency relationship of a typical handpiece in this relatively lightly loaded pre-surgery condition is illustrated in FIG. 1. The maximum recorded admittance ($Y_s$) corresponds to the series resonance ($f_s$) and the minimum admittance ($Y_p$) corresponds to the parallel resonance ($f_p$). Driving the handpiece with a power signal at the series resonance results in the most efficient conversion of electrical to mechanical energy because the electrical series resonance occurs at the same frequency as the mechanical resonance.

Figure 2:
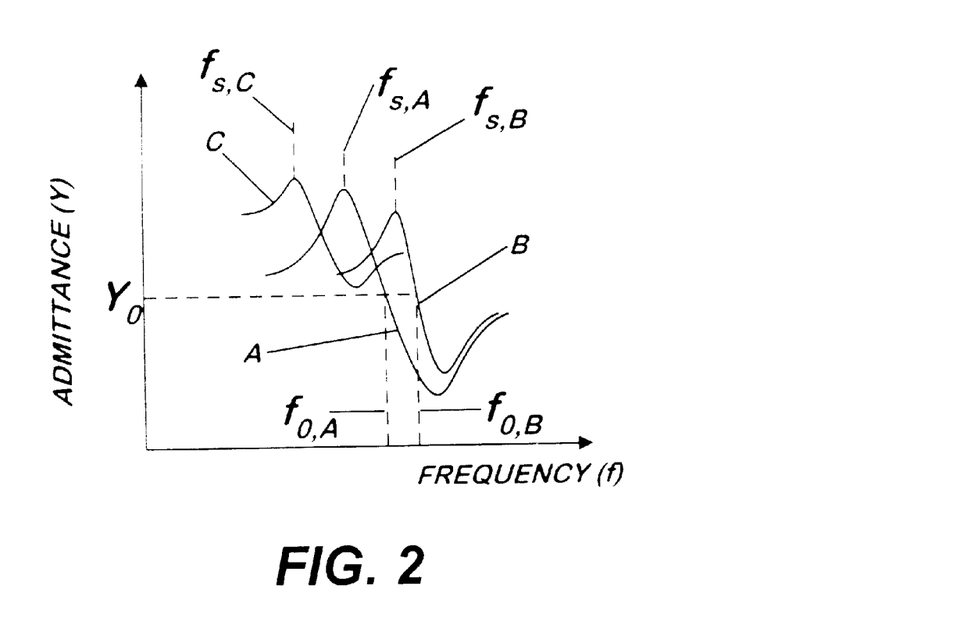
FIG. 2 a graph of admittance versus frequency illustrating the way in which the response of a typical ultrasonic handpiece may shift when the handpiece is subjected to mechanical and thermal loading.

However, when the handpiece is mechanically loaded, as during surgery, the shape and position of the admittance versus frequency curve changes and thus the characteristic series and parallel resonant frequencies change. Curve "A" in FIG. 2 represents the characteristic admittance versus frequency curve shown in FIG. 1 for a lightly loaded handpiece. Curve "B" represents, for example, the admittance v. frequency curve when the same handpiece is mechanically loaded. As can be seen, curve "B" has shifted right ($f_{s,B} > f_{s,A}$) and the maximum admittance of curve "B" is lower than the maximum admittance of curve "A," and the minimum admittance of curve "B" is higher than the minimum admittance of curve "A." Certain mechanical loading conditions can also shift curve "A" toward lower frequencies (to the left).

Curve "C" represents the admittance v. frequency curve for the same handpiece when the temperature of the crystal within the handpiece has increased somewhat over room temperature. Curve "C" has shifted generally upward and leftward (i.e., higher admittance and lower frequency values) relative to curve "A." If the power signal were delivered to the handpiece at the originally determined series resonance, for example, the efficiency of the power signal drops off dramatically. Thus, subjecting the handpiece to loading without adjusting the frequency of the power signal reduces the efficiency and predictability of the power signal.

One approach to tuning a handpiece in real time during surgery employs using a power signal at a frequency that is the average of the series and parallel resonant frequencies in the relatively unloaded pre-surgery condition and adjusts the frequency of the power signal so that a constant admittance is maintained. This type of system is more fully described in U.S. Pat. No. 5,431,664 ("the '664 patent"), which is incorporated by reference. Briefly, systems of this type tune the handpiece based on a constant admittance value ($Y_0$), which is determined as the average of the maximum and minimum admittances by the equation $$Y_0 = \frac{(Y_s + Y_p)}{2}.$$

(Some commercially available constant-admittance control systems fix $Y_0$ at a point other than the average, for example, $Y_0 = 0.3Y_s + 0.7Y_p$.) As the handpiece is loaded under many types of conditions, the admittance v. frequency curve shifts along the frequency axis. Such a shift is shown, for example, by curve "A" and curve "B" in FIG. 2, with curve "B" representing a possible response of a handpiece to mass reactive loading. The control system described in the '664 patent adjusts the frequency of the drive signal to maintain the admittance at $Y_0$.

While this type of tuning and control system is effective over a relatively broad range of loading conditions, the handpiece is never operated at the series resonance and thus some efficiency is lost. Moreover, shifts in the admittance versus frequency curves along the admittance axis, such as those shown by curve "C" in FIG. 2, may render this type of constant-admittance control system ineffective. The tuning admittance ($Y_0$) is not found on any portion of curve "C," which may describe the response of a mechanically loaded and heated handpiece. Control systems that adjust the drive frequency to coincide with the series resonance typically use phase locked loop circuits with very narrow tuning ranges.

Another approach to tuning and controlling an ultrasonic handpiece relies on the use of a broad-band, substantially constant-amplitude calibration signal to determine the response of the handpiece to real-time mechanical loading. Such a system is described in U.S. patent application Ser. No. 08/769,257 filed Dec. 18, 1996 ("the '257 application"), which is incorporated in this document in its entirety by this reference. Briefly, a broad-band calibration signal is fed to an ultrasonic handpiece, and the response of the handpiece is determined by a fast fourier transform digital signal analyzer. Aspects of the drive signal and perhaps the calibration signal are altered based on the response of the handpiece. This broad-band approach generates detailed information about the shape of the admittance versus frequency response curve for a particular handpiece. However, such detailed information may not be required in order to effectuate tuning and control of the handpiece.

Thus, a need continues to exist for a method and control system capable of tuning an ultrasonic handpiece to its series resonance when the handpiece is subjected to widely varying load conditions.

SUMMARY OF THE INVENTION

The present invention improves upon prior art methods of tuning and controlling ultrasonic devices by automatically tuning the handpiece before a surgical procedure and exciting the handpiece with a dithered drive signal during surgery. Before being subjected to loads during surgery, the handpiece is excited with a series of single-frequency signals over a tuning range of frequencies broad enough to encompass all expected values of the series and parallel resonances. The incremental difference between each successive single-frequency signal is small enough to result in sufficient resolution of the handpiece response. This incremental difference is significantly less than the expected difference between the series resonance and the parallel resonance of the handpiece (or the bandwidth of the handpiece). For example, a difference of about 10 Hz would be sufficient for a typical handpiece with a bandwidth of a few hundred hertz.

The response of the handpiece is measured by a digital signal processor ("DSP") as the admittance corresponding to each of these tuning frequencies. The DSP records the series of admittance values at all the tuning frequencies in order to determine the admittance versus frequency relationship for the handpiece over the entire tuning frequency range. The series resonance corresponds to the frequency at which maximum admittance occurs and the parallel resonance corresponds to the frequency at which minimum admittance occurs. Alternatively, the frequency response of each handpiece may be determined using a fast fourier transform analysis, as described for example in the '257 application.

In a first embodiment of the invention, at time to and after the tuning procedure is performed, the drive signal has a frequency, $f_0$, equal to the series resonance $f_s$. The response of the handpiece at $t_0$, measured as the admittance ($Y_0$), is recorded. At time $t_1$, $f_1$ equals $f_0$ plus a dither increment, $\delta$. The response of the handpiece, $Y_1$, is measured and compared to the previous response, $Y_0$. The next frequency and all later frequencies of the drive signal, $f_{2 \to \infty}$, are determined according to the following equation:

$$f_{n+1} = f_n + \delta[\text{sign}(f_n - f_{n-1})(\text{sign}(Y_n - Y_{n-1})],$$

where
n>2 and
sign(x) =1 if x≧0, else sign(x)=−1.

The accuracy with which this embodiment of the invention can track the series resonance is largely determined by how often the frequency is changed by $\delta$. The more often the frequency is changed, the smaller $\delta$ may be and the more closely $f_n$ will correspond to the actual value of the series resonance. Instead of varying the frequency by a constant amount ($\delta$) at each time increment, a proportional-integral-differential control algorithm may be used to determine, not only $f_{n+1}$, but also the corresponding drive voltage, $V_{n+1}$, and the dither increment. As a fail safe mechanism, the system can check $|f_{n+1} - f_0|$ to determine if that difference is greater than a predetermined threshold. While the value of this threshold varies depending upon the types of loading conditions to which the handpiece is exposed, typical values for the threshold are about 1 to 10 times the bandwidth of the handpiece as measured in an unloaded condition. If $|f_{n+1} - f_0|$ is greater than this threshold, the control system would assume that the control logic had failed and it would reinitiate the pre-surgery tuning procedure in order to determine accurately the actual series resonance. The system would then reset $f_0 = f_s$ and restart the frequency control routine.

In a second embodiment of the invention, after the pre-surgery tuning procedure is performed, the drive signal that is fed to the handpiece is dithered to alternate among a power signal at a first frequency (the series resonance as determined during the tuning procedure) and at least two calibration components at calibration frequencies that differ from the first frequency by $\delta$ or multiples of $\delta$. Because $\delta$ is very small in comparison to the difference between the series and parallel resonances, the calibration components are almost as effective in driving the handpiece as the power signal (and perhaps even more effective under some circumstances). The dither increment, $\delta$, used in this embodiment may or not be equal to the dither increment used in the first embodiment of the invention discussed above. The calibration frequencies include at least one frequency which is less than the first frequency and at least one frequency which is greater than the first frequency. Essentially, a scaled-down version of the pre-surgery tuning procedure is repeatedly performed at frequencies immediately surrounding the last known value of the series resonance.

The admittance of the handpiece at each discrete frequency (the first frequency and each of the calibration frequencies) is measured and the set of responses is analyzed to determine the probable new value of the series resonance. Once the new series resonance is determined, an appropriate control signal is generated to alter the first frequency so that it corresponds to the series resonance. The number of calibration components, the dither increment, the amplitude of the calibration components, and the order in which the drive signal sweeps through the calibration components and power signal may be varied to optimize the effectiveness of the control system.

It is accordingly an object of the present invention to provide a control system and method that performs real-time analysis of the frequency response of a mechanically loaded ultrasonic handpiece in order to estimate at least the series resonance of the handpiece and to adjust continuously at least the frequency of a power signal fed to the handpiece.

It is a further object of the present invention to provide a tuning system that quickly and accurately measures the response of an ultrasonic handpiece to a range of frequencies broad enough to encompass all potential values of the series and parallel resonances in order to determine the characteristic admittance versus frequency response of the handpiece.

Other objects, features and advantages of the present invention will become apparent with reference to the drawings and the following description of the drawings and claims.

DETAILED DESCRIPTION OF THE DRAWINGS

Before a surgical procedure is started, the system and method according to the present invention is used to tune the ultrasonic handpiece as described above. Specifically, a voltage-controlled oscillator ("VCO") drives the handpiece with a series of single-frequency signals at a substantially constant amplitude, and a DSP measures the response of the handpiece to each single-frequency signal. The range of frequencies through which the VCO sweeps (the tuning frequency range) may be defined as any portion of a spectrum from 25 kHz to 80 kHz, which is the operating spectrum for typical existing ultrasonic handpieces currently used in eye surgery. A range of approximately 100 Hz to 10,000 Hz is suitable as the tuning frequency range and that about 4,000 Hz is preferable. Such values of the tuning frequency range are broad enough to encompass virtually all potential values of $f_s$ and $f_p$. Other tuning frequency ranges may be more appropriate for other ultrasonic applications, and the overall operation of the systems and methods described in this document would be equally useful for tuning and control of handpieces used in those applications.

When used to control the handpiece during a surgical procedure, the system and method of the present invention generally employs a VCO combined with an amplifier as a source to generate the signal that drives an ultrasonic handpiece ("the drive signal"). The frequency of the drive signal is altered by a dither increment from the last known estimate of the series resonance ("the power frequency"). Some embodiments of the present invention dither the drive signal above and below the power frequency and others dither the power signal in only one direction (above or below the power frequency) based on the response of the handpiece to earlier dithered drive signals. For at least some systems according to the present invention, the VCO is programmable and thus easily adjustable by varying certain input information fed to the VCO. A digital signal processor ("DSP") may be used to measure the response of the handpiece to each component of the drive signal (those at the power frequency and those at the dithered frequencies) and compare those responses to determine the probable value of the actual series resonance. The output of the DSP is used to generate control parameters embodied within an appropriate control signal, which is fed to the VCO in order to alter aspects of the drive signal.

Figure 3:
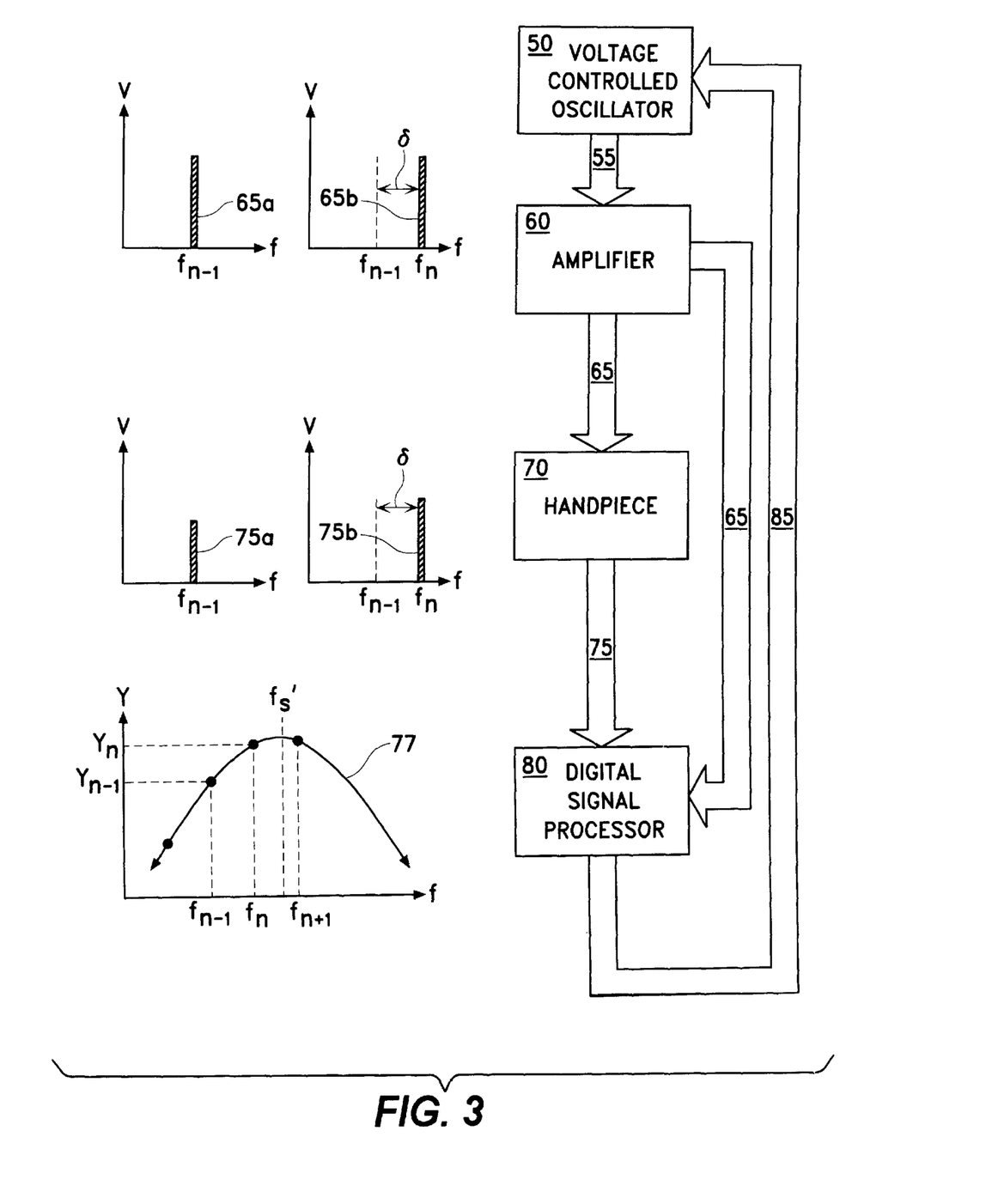
FIG. 3 is a block diagram of a preferred embodiment of a system and method for tuning and controlling an ultrasonic handpiece during a surgical procedure according to the present invention with accompanying graphical representations of electrical signals generated by each component.

FIG. 3 is a block diagram illustrating a preferred embodiment of a system according to the present invention for tuning and controlling an ultrasonic handpiece 70. The system illustrated in FIG. 3 determines whether the series resonance is likely increasing or decreasing and adjusts the frequency of power signal 65 to follow the change in the series resonance. The system illustrated in FIG. 3 accomplishes this result by examining the response (response signals 75a and 75b) of handpiece 70 (measured as admittances $Y_{n-1}$ and $Y_n$) at the previous ($f_{n-1}$) and current ($f_n$) frequencies of the power signals 65a and 65b respectively. The difference between $f_{n-1}$ and $f_n$ is the dither increment, δ, which may be a constant value or may vary depending on the response of handpiece 70.

In the embodiment shown in FIG. 3, the combination of VCO 50 and amplifier 60 generates drive signal 65, which is a variable signal that changes incrementally from drive signal 65a to 65b at frequencies $f_{n-1}$ and $f_n$ respectively. Each of drive signals 65a and 65b is preferably of approximately equal amplitude but may have unequal amplitude depending on whether the drive signal 65 is controlled using a constant current or a constant admittance control system. The frequency $f_{n-1}$ corresponds approximately to the last known estimate of series resonance $f_s$. In the example shown in FIG. 3, frequency $f_n$ is greater than $f_{n-1}$ by dither increment δ, but under appropriate circumstance $f_n$ could be less than $f_{n-1}$.

The frequencies of response signals 75a and 75b correspond to the frequencies of drive signals 65a and 65b. In the example shown in FIG. 3, the amplitude of response signal 75a is less than the amplitude of response signal 75b. Drive signal 65a and response signal 75a are fed synchronously to DSP 80. DSP 80 divides the current of response signal 75a by the voltage of drive signal 65a (after perhaps each is attenuated to protect the input section of DSP 80) to determine the admittance $Y_{n-1}$ at its corresponding frequency $f_{n-1}$ and this admittance value is stored. Similarly, DSP 80 determines the admittance $Y_n$ at $f_n$ by dividing the current of response signal 75b by the voltage of drive signal 65b. The points $(Y_{n-1}, f_{n-1})$ and $(Y_n, f_n)$ lie along admittance curve 77, which is a representation of the admittance versus frequency relationship that may be exhibited by handpiece 70. The peak of admittance curve 77 defines the actual value of the series resonance $f_s'$.

Figure 4:
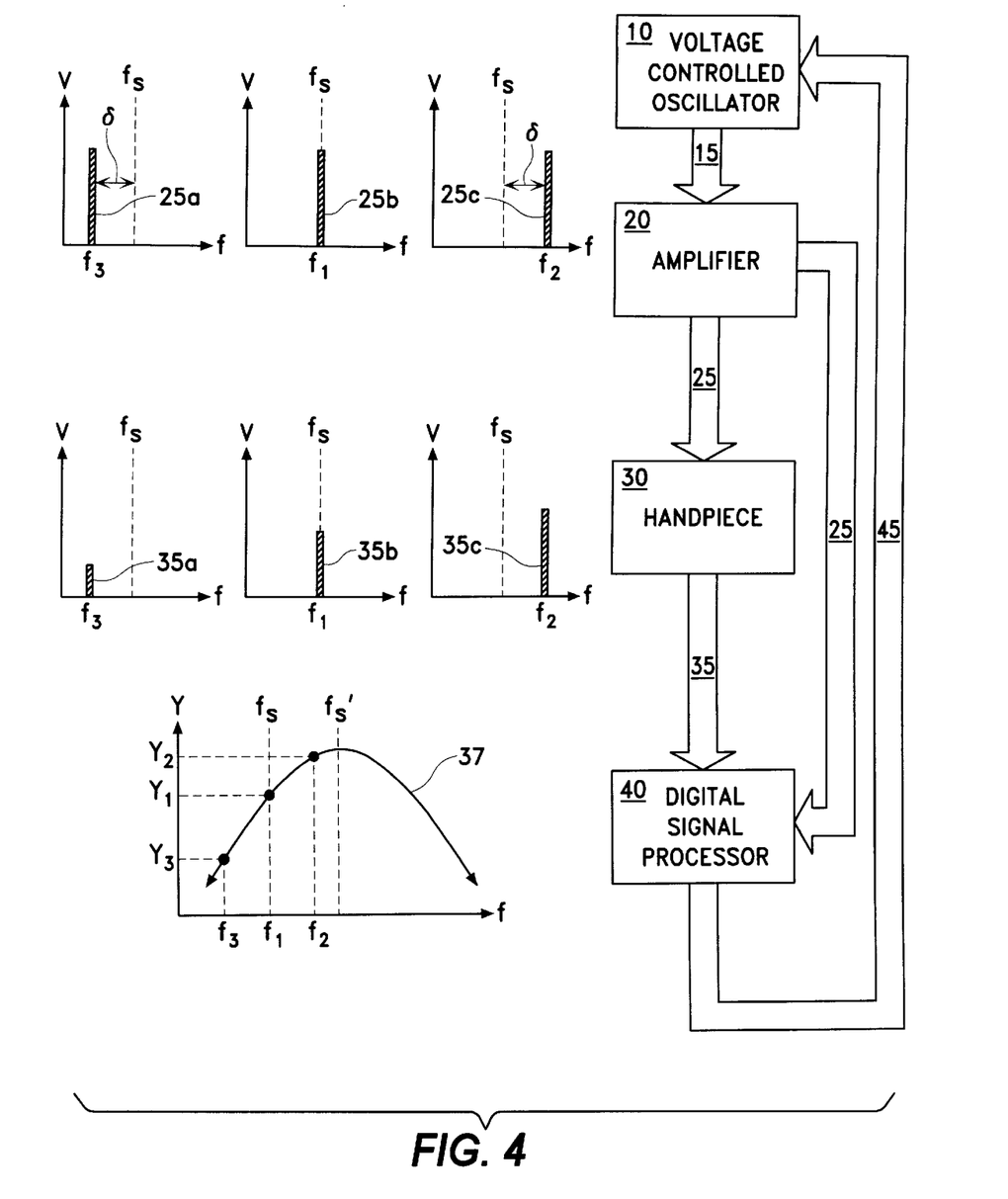
FIG. 4 is a block diagram of an alternate embodiment of a system and method for tuning and controlling an ultrasonic handpiece during a surgical procedure according to the present invention with accompanying graphical representations of electrical signals generated by each component.

For example, the actual series resonance $f_s'$ shown in FIG. 3 is greater than either $f_{n-1}$ or $f_n$. Under these conditions, the control logic programmed into DSP 80 would determine that $f_{n+1}$ should be increased by the dither increment and send an appropriate control signal 85 to VCO 50 in order to effectuate this increase. However, admittance curve 77 as shown in FIG. 4 is only one possible scenario that may be encountered. The logic implemented by DSP 80, which responds appropriately to any shift in the admittance v. frequency curve, is defined by the following equation:

$$f_{n+1} = f_n + \delta[\text{sign}(f_n - f_{n-1})(\text{sign}(Y_n - Y_{n-1}))],$$

where $n \geq 2$ and $\text{sign}(x) = 1$ if $x \geq 0$, else $\text{sign}(x) = 1$.

Of course, the control system according to this embodiment of the invention may also calculate $f_{n+1}$ based on more than the last two points along admittance curve 77. In theory, the more data used to determine $f_{n+1}$, the more closely $f_{n+1}$ will track $f_s'$. One skilled in the art will recognize that depending upon the nature of the external loading and how fast the data are obtained, it may be beneficial to analyze more than the last two data points. The accuracy with which the control system shown in FIG. 3 can track series resonance is largely determined by how often the control system can poll and update the power frequency. The dither increment is a function of the rate of change of the series resonance and the duty cycle, $P_{ctrl}$, of the control system (the duty cycle is the inverse of the frequency with which the control system polls and updates the power frequency). The equation defining the dither increment is:

$$\delta \geq \left(\frac{df_s}{dt}\right) P_{ctrl}.$$

For example, when the series resonance could change as much as 600 Hz in 100 ms and the duty cycle of the control system is 1 ms, then the dither increment should be at least 6 Hz. The resulting error $f_e$ in tracking the actual series resonance is approximately related to the dither increment as follows: $f_e = 2\delta$. To reduce the magnitude of $f_e$, $\delta$ should be small compared to the bandwidth of the handpiece, preferably about 0.1 $(f_p - f_s) \geq \delta \geq 0.001$ $(f_p - f_s)$, and more preferably about 0.01 $(f_p - f_s)$. Thus, the duty cycle, $P_{ctrl}$, should be as short as possible. In the example discussed immediately above in which $P_{ctrl}$ is 1 ms, the 6 Hz dither increment, which is about ⅕₀th of a typical handpiece bandwidth of 300 Hz (0.02 times the typical bandwidth), would result in control of the handpiece sufficient to keep the power frequency within a range near the series resonance of approximately ±4% of the bandwidth. If, however, $P_{ctrl}$ is 10 ms, then $\delta$ would equal 60 Hz and the power frequency would fall within a range near the series resonance of about ±40% of the bandwidth. Thus, the shorter $P_{ctrl}$, the more accurately the control system can track series resonance. A shorter duty cycle would also allow the use of a handpiece with a narrower bandwidth, which is typically more efficient at converting electrical into mechanical energy.

The control system shown in FIG. 3 may also vary the voltage of drive signal 65 depending upon the admittance of handpiece 30. A corresponding decrease in admittance generally indicates a reduction in the efficiency of the handpiece (a reduction in the power factor) and a decrease in the stroke of handpiece 30. Such stroke reductions can occur, for example, due to mechanical loading of handpiece 30 or slow frequency compensation of drive signal 65 (which results in a greater average difference between the frequency of the drive signal and the series resonance). To maintain the cutting ability of handpiece 30 (which is directly related to its stroke), the power delivered to handpiece 30 is increased by increasing the voltage of drive signal 65. Thus, as admittance decreases, the voltage of drive signal 65 is increased.

One possible manner in which the voltage of drive signal 65 may be controlled is to implement logic within DSP 80 to maintain the current, I, of drive signal 65 constant. In such a system $I = (Y)(V)$, where Y is the measured admittance of handpiece 70 (determined by DSP 80 dividing the current of signal 75 by the voltage of drive signal 65) and V is the voltage of drive signal 65. Under load conditions that cause Y to decrease, I would also decrease absent an adjustment to V. In order to maintain current, 1, of drive signal 65 constant, the voltage of drive signal 65 is increased. Conventional PID control logic can be applied within DSP 80 to perform all calculations and make adjustments to V in order to keep I constant. Such PID control logic would compensate for any delay in the response of handpiece 70 that would cause the current of signal 75 to change after the voltage of drive signal 65.

The control system shown in FIG. 3 may also vary the dither increment, depending upon the last change in the admittance, $|Y_n - Y_{n-1}|$. In general, the greater the change in the admittance, the greater the dither increment (i.e., $\delta \alpha |Y_n - Y_{n-1}|$). A small initial value for $\delta$ will generally reveal the direction in which the series resonance is shifting. After this initial direction is determined, $\delta$ may be increased in order to enable faster compensation for later frequency shifts. However, if the nature of the shifts in series resonance is such that several arbitrary shifts in series resonance occur, then a constant, relatively small, value for $\delta$, would be more useful. If $\delta$ is varied, those variations $\delta$ and changes to the voltage of drive signal 65 may be implemented using, for example, well known PID control logic. It is possible to "customize" system response to a certain handpiece type or surgical technique. For example, if the handpiece is loaded only occasionally such that the series resonance shifts downward approximately 200–300 Hz, the control system may assume that any load sensed requires a shift in series resonance of about 200–300 Hz, with closed-loop control of the loaded handpiece as described above after the initial shift.

Under some circumstances, the control system shown in FIG. 3 may fail to track the series resonance closely enough. A correction routine prevents such a failure from unacceptably compromising the effectiveness of handpiece 30. If $|f_{n+1} - f_0|$ were ever found to be greater than a predetermined threshold, then the control system would assume that the control logic had failed. Upon discovering such a failure, the control system would reinitiate the pre-surgery tuning procedure in order to determine accurately the actual series resonance. The system would then reset $f_0$ to $f_s$ and restart the frequency control routine.

FIG. 4 is a block diagram that illustrates a second embodiment of a system according to the present invention for tuning and controlling an ultrasonic handpiece. The operation of the system and performance of the method illustrated in FIG. 4 results in the determination of the characteristic response of handpiece 30 at a set of discrete frequencies (e.g., $f_3$ and $f_1$) relatively near and including the power frequency, $f_2$ (which approximates the last known value of the series resonance $f_s$). In the embodiment shown in FIG. 4, the combination of VCO 10 and amplifier 20 generates drive signal 25, which is a variable signal that sweeps through drive signals 25a, 25b, and 25c in succession at frequencies $f_1$, $f_2$, and $f_3$ respectively. Each of drive signals 25a, 25b, and 25c are preferably of approximately equal amplitude. The frequency $f_2$ corresponds approximately to the last known value of series resonance $f_s$, frequency $f_1$ is less than $f_2$, and $f_3$ is a frequency greater than $f_2$. Preferably, $f_1$ and $f_3$ differ from $f_2$ by a dither increment ($\delta$), and the preferred dither increment is defined as about 0.1 ($f_p$–$f_s$) $\geq \delta \geq 0.001$ ($f_p$–$f_s$), and more preferably about 0.01 ($f_p$–$f_s$).

Because drive signal 25 sweeps through drive signals 25a, 25b, and 25c, the frequency of response signal 35 of handpiece 30 also varies as shown by response signals 35a, 35b, and 35c. In the example shown in FIG. 4, the amplitude of response signal 35a is less than the amplitude of response signal 35b, which is in turn less than the amplitude of response signal 35c. Drive signals 25a, 25b, and 25c and response signals 35a, 35b, and 35c are fed synchronously to DSP 40 (after perhaps each is attenuated to protect the input section of DSP 40). DSP 40 divides the current of response signals 35a, 35b, and 35c by the voltage of drive signals 25a, 25b, and 25c respectively in order to determine admittance values $Y_1$, $Y_2$, and $Y_3$ at their corresponding frequencies $f_1$, $f_2$, and $f_3$. The points $(Y_1, f_1)$; $(Y_2, f_2)$; and $(Y_3, f_3)$ lie along admittance curve 37, which is a representation of the admittance versus frequency relationship that may be exhibited by handpiece 30. The peak of admittance curve 37 defines the actual value of the series resonance $f_s'$.

The actual series resonance $f_s'$ shown in FIG. 4 is, for example, greater than either of the calibration frequencies ($f_1$ and $f_3$) and the power frequency ($f_2$). Under these conditions the control logic programmed into DSP 40 would determine a new drive frequency to be $f_2+\delta$ (i.e., $f_3$) or, for example, $f_2$ plus a different increment based on the original shape of the admittance curve. DSP 40 then generates and sends an appropriate control signal 45 to VCO 10 in order to alter the frequency of drive signal 65. The calibration frequencies $f_1$ and $f_3$ would also be increased so that they continue to differ from $f_2$ by the dither increment $\delta$. However, admittance curve 37 as shown in FIG. 4 is only one possible scenario that may be encountered.

Figure 5A:
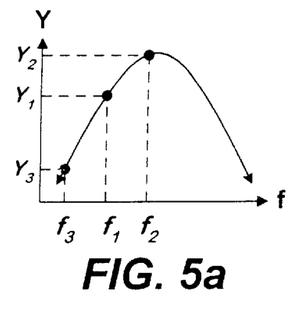
FIGS. 5a–5i is a series of graphs of the portion of the admittance versus frequency response curves in the vicinity of the series resonance on which the admittance responses corresponding to two calibration frequencies and the power frequency are marked to illustrate one type of logic which may be used by the control system shown in FIG. 4 to estimate the series resonance of a mechanically loaded handpiece.
Figure 5B:
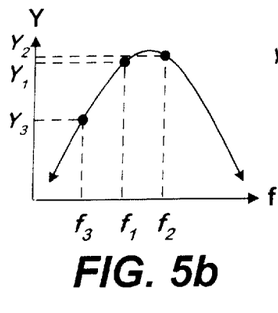
Figure 5C:
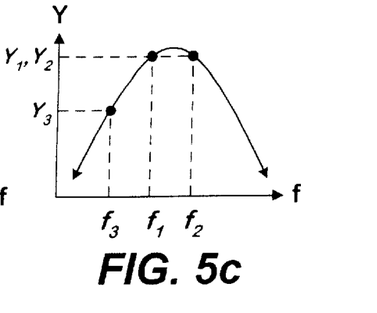
Figure 5D:
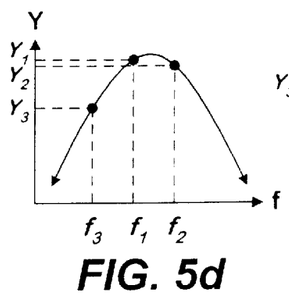
Figure 5E:
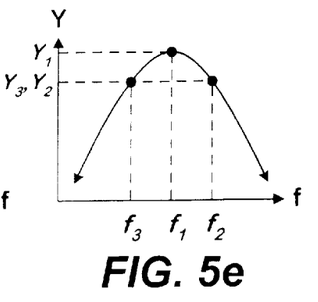
Figure 5F:
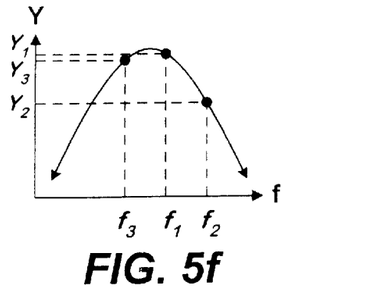
Figure 5G:
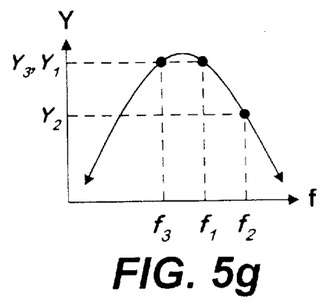
Figure 5H:
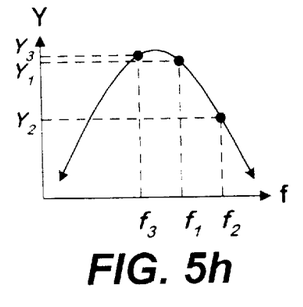
Figure 5I:
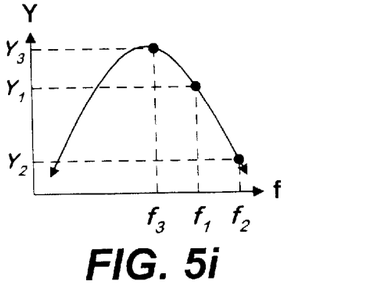

FIGS. 5a–5i are qualitative representations of all possible admittance versus frequency curves that may be encountered by the control system shown in FIG. 4. FIGS. 5a–5d represent the cases in which $f_2$ must be increased to approximate $f_s'$. The greatest adjustment to $f_2$ is required for the situation represented in FIG. 5a and progressively less adjustment to $f_2$ is required in FIGS. 5b, 5c, and 5d. FIG. 5e represents the case in which $f_2$ requires no adjustment. FIGS. 5f–5i represent cases in which $f_2$ must be decreased to approximate $f_s'$ with progressively more adjustment to $f_2$ required in FIGS. 5f, 5g, 5h, and 5i. Of course, a system according to the present invention may employ more than two calibration components with an accompanying change in control logic. The table below summarizes the logic applied by DSP 40 (using two calibration components, drive signals 25a and 25c, along with drive signal 25b) in order to adjust $f_2$ so that it corresponds approximately to $f_s'$:

| Condition | Action |
| --- | --- |
| $Y_1 < Y_2 < Y_3$ or $Y_1 < Y_2 = Y_3$ or $Y_1 < Y_3 < Y_2$ | Increase $f_2$ |
| $Y_1 = Y_3 < Y_2$ | Maintain $f_2$ at current value |
| $Y_3 < Y_2 < Y_1$ or $Y_3 < Y_1 < Y_2$ or $Y_3 < Y_1 = Y_2$ | Decrease $f_2$ |

The amount by which $f_2$ is adjusted is determined by comparing the slope of each line defined by adjacent points on the admittance curve 37. For example, the first and second derivatives of curve 37 (i.e., of the function Y(f)) may be approximated in a control system using a constant dither increment, $\delta$, using the three points $(Y_1, f_1)$; $(Y_2, f_2)$; and $(Y_3, f_3)$ as follows:

$$\frac{dY}{df} \cong \frac{Y_2 - Y_3}{2\delta} \text{ and } \frac{d^2Y}{df^2} \cong \left(\frac{Y_2 + Y_3 - 2Y_1}{\delta^2}\right) \text{ where } \delta = f_2 - f_1 = f_1 - f_3$$

The first and second derivatives of Y(f) in a system in which $\delta$ varies are approximated according to the following equations:

$$\frac{dY}{df} \cong \frac{Y_3 - Y_2}{f_3 - f_2} \text{ and } \frac{d^2Y}{df^2} \cong \left(\frac{Y_3 - Y_2}{f_3 - f_2} - \frac{Y_2 - Y_1}{f_2 - f_1}\right) / f_2 - f_1$$

The system described above employs the minimum number of data points, three, needed to approximate first and second derivatives of Y(f). Increasing the number of calibration frequencies would, of course, increase the number of data points available for determining accurately the first and second derivatives of Y(f) thus enabling a better estimate of the actual series resonance. However, the time delays inherent in the process of gathering and analyzing more than three data points reduces the accuracy of the analysis because individual data points might reflect the location of a point on curve 37 after curve 37 has already shifted. The optimum number of data points for best determining the shape of curve 37 depends on the time delay between power signal 25b and calibration signals 25a and 25c and the time delay caused by DSP 40 analyzing the data points along the admittance curve 37. The longer either time delay, the lower the optimum number of data points (with a minimum of three data points). As similarly discussed above in connection with DSP 80 of the control system shown in FIG. 3, DSP 40 of the control system shown in FIG. 4 may implement logic to alter the dither increment or the drive signal voltage or both depending upon the shape and amplitude of admittance curve 37.

DSP 40 or DSP 80 may be a multi-purpose, programmable processor of which commercial examples are available. For example, Stanford Research Systems at 1290-D Reamwood Avenue, Sunnyvale, Calif. 94089, currently sells two fast fourier transform (FFT) DSP's, the Model SR760 and Model SR770 having a single input channel. Stanford Research markets a two-channel, FFT Signal Analyzer suitable for use as DSP 40 or DSP 80, the Model SR780. All these Stanford Research DSP's have real-time bandwidths of at least 100 kHz and dynamic range of 90 dB and have fully programmable center frequency, bandwidth, analysis routines, and output. All three DSP's may be programmed by using the interface supplied (a series of menu-driven options shown on an integral display) or by using a separate computer able to output commands over a standard RS-232 or GPIB interface. The dual-input capability of the SR780 allows it to be programmed to perform mathematical comparisons between two input signals.

After DSP 40 or DSP 80 estimates the value of $f_s'$, it may also be programmed to apply proportional-integral-differential ("PID") logic in order to generate control parameters embodied within control signal 45. The use of PID logic is the best way to prevent over-compensation of the drive frequency and to reduce the potential that unstable oscillations in drive frequency are caused by the control system shown in FIGS. 3 and 4. Moreover, well known control logic other than PID logic may also be used to adjust drive frequency for changes in $f_s'$ depending upon the demands placed on the control system by the types of loading conditions likely encountered by an ultrasonic handpiece. For example, the system may require only the use of proportional or proportional-integral control. The nature of PID and other control logic is well known and thus not described further in this document.

Because the use of software implemented PID logic (within DSP 40 or DSP 80) may result in an unacceptable delay in the control systems shown in FIGS. 3 and 4, a special purpose, digital PID controller may be inserted in the control system at the output of DSP 40 or DSP 80. Such a digital PID controller would perform PID logic on the output of DSP 40 or DSP 80 and generate control signal 45 or 85 respectively. Such a PID controller may be any one of a number of commercially available integrated circuits or discrete components arranged in any one of many widely known configurations. Whether control signal 45 or 85 is generated directly by a DSP or through a suitable digital PID controller, VCO 10 or VCO 50 preferably uses control signal 45 or 85 to adjust $f_1$ so that it corresponds approximately to the newly discovered $f_s'$ under load. The entire cycle is repeated continuously to maintain $f_1$ at approximately the actual series resonance of the handpiece.

The Stanford Research SR780 also contains a programmable source that is sufficiently flexible to generate drive signal components 25*a*, 25*b*, and 25*c* or 65*a* and 65*b*. Thus, the SR780 is capable of being programmed to provide drive signal 25 or 65, measure response signals 35*a*, 35*b*, 35*c* 75*a*, or 75*b*, determine admittance curve 37 or 77 and the value of $f_s'$, and generate control signal 45 or 85 in order to alter drive signal 25 or 65 (and hence drive signals 25*a*, 25*b*, and 25*c* or drive signals 65*a* and 65*b*) to compensate for a mechanical and/or thermal load encountered by a handpiece in use.

While certain embodiments of the present invention have been described above, these descriptions are given for purposes of illustration and explanation. Variations, changes, modifications and departures from the systems and methods disclosed above may be adopted without departure from the scope or spirit of the present invention which, in sum, employs a source to generate a drive signal which is dithered, either in one direction based on a trend established by past values of frequency and admittance or in both directions to determine the response of the handpiece at frequencies immediately surrounding the last known value of the series resonance, as a means of compensating for changes in the operating characteristics of the handpiece while in use.

I claim:

1. A method of controlling an ultrasonic handpiece having a variable series resonance frequency, comprising the steps of:
   a) generating a drive signal having,
      i. a first signal at a first frequency substantially equal to a known current value of a series resonance frequency,
      ii. a second signal at a second frequency greater than the first frequency and
      iii. a third signal at a third frequency less than the first frequency;
   b) exciting the handpiece with the drive signal;
   c) measuring a first admittance at the first frequency, a second admittance at the second frequency, and a third admittance at the third frequency;
   d) predicting a future series resonance frequency based on the relative values of the first admittance, the second admittance, and the third admittance; and
   e) changing the first frequency by a dithering increment equal to the absolute value of the difference between the second frequency and the first frequency.

2. The method of claim 1, in wherein the step of changing the first frequency further comprises:
   a. reducing the first frequency if:
      i. the third admittance is less than the first admittance and the first admittance is less than or equal to the second admittance or
      ii. the third admittance is less than the second admittance and the second admittance is less than the first admittance;
   b. maintaining the first frequency substantially constant if the third admittance substantially equals the second admittance and the third and second admittances are less than the first admittance; and
   c. increasing the first frequency if:
      i. the second admittance is less than the third admittance and the third admittance is less than or equal to the first admittance or
      ii. the second admittance is less than the first admittance and the first admittance is less than the third admittance.

3. The method of claim 2, in which each of the reducing and increasing steps further comprises determining the dithering increment by which the first frequency is reduced or increased, respectively.

4. The method of claim 3, in which the dithering increment is between approximately 0.001 and 0.1 times the difference between an initial value of a series resonance frequency and an initial value of a parallel resonance frequency of the handpiece.

5. The method of claim 4, in which the dithering increment is approximately 0.01 times the difference between the initial value of the series resonance and the initial value of the parallel resonance of the handpiece.

6. The method of claim 3, further comprising the step of adjusting the dithering increment.

7. A method of controlling during a surgical procedure an ultrasonic phacoemulsification handpiece having a characteristic unloaded series resonance frequency, comprising the steps of:
   a) generating a first drive signal at a first frequency substantially equal to the unloaded series resonance frequency of the handpiece;
   b) exciting the handpiece with the first drive signal;
   c) measuring a first admittance at the first frequency;
   d) determining a second frequency that differs from the first frequency by a dithering increment;
   e) generating a second drive signal at the second frequency;
   f) exciting the handpiece with the second drive signal;
   g) measuring a second admittance at the second frequency;

h) predicting a future series resonance frequency at a third frequency based on a comparison of the first admittance to the second admittance and the first frequency to the second frequency;

i) setting the first frequency equal to the second frequency and the first admittance equal to the second admittance;

j) setting the second frequency equal to the third frequency; and k) repeating steps e–j until the surgical procedure is completed.

8. The method of claim 7, in which the determining step further comprises:

i. setting the third frequency to a value greater than the second frequency if:

A. the second admittance is less than the first admittance and the first frequency is less than the second frequency or         B. the second frequency is greater than or equal to the first frequency and the second admittance is greater than or equal to the first admittance; or     ii. setting the third frequency to a value less than the second frequency if:

A. the second admittance is less than the first admittance and the first frequency is greater than or equal to the second frequency or         B. the second admittance is greater than or equal to the first admittance and the second frequency is less than the first frequency.

\* \* \* \* \*